US008183208B2

(12) United States Patent
Faulk (10) Patent No.: US 8,183,208 B2
(45) Date of Patent: May 22, 2012

(54) TARGETED DELIVERY OF DRUGS FOR THE TREATMENT OF VIRAL INFECTIONS (75) Inventor: W. Page Faulk, Indianapolis, GA (US)

(73) Assignee: Faulk Pharmaceuticals, Inc., St. Simons Island, GA (US)

( * ) Notice: Subject to any disclaimer, the term of this patent is extended or adjusted under 35 U.S.C. 154(b) by 228 days.

(21) Appl. No.: 11/968,904

(22) Filed: Jan. 3, 2008

(65) Prior Publication Data
US 2008/0103094 A1    May 1, 2008

Related U.S. Application Data (63) Continuation of application No. 10/477,997, filed as application No. PCT/US02/11892 on May 15, 2002, now abandoned.

(60) Provisional application No. 60/290,668, filed on May 15, 2001, provisional application No. 60/355,394, filed on Feb. 8, 2002.

(51) Int. Cl.
A61P 43/00    (2006.01)

(52) U.S. Cl. ............... 514/18.9; 424/9.2; 424/204.1

(58) Field of Classification Search .................. None
See application file for complete search history.

(56) References Cited

U.S. PATENT DOCUMENTS

| | | | |
|---|---|---|---|
| 4,886,780 A | 12/1989 | Faulk | |
| 4,895,714 A | 1/1990 | Faulk | |
| 5,000,935 A | 3/1991 | Faulk | |
| 5,087,616 A | 2/1992 | Myers et al. | |
| 5,108,987 A | 4/1992 | Faulk | |
| 5,122,368 A * | 6/1992 | Greenfield et al. | 424/85.2 |
| 5,208,323 A * | 5/1993 | Page et al. | 530/391.9 |
| 5,238,940 A | 8/1993 | Jiang et al. | |
| 5,268,165 A | 12/1993 | Hedlund et al. | |
| 5,326,778 A | 7/1994 | Rosebrough | |
| 5,688,488 A | 11/1997 | Low et al. | |
| 5,906,977 A | 5/1999 | Sinn et al. | |
| 6,066,319 A | 5/2000 | Halperin et al. | |
| 6,190,661 B1 | 2/2001 | Kelley et al. | |
| 6,310,039 B1 | 10/2001 | Kratz | |
| 6,548,531 B2 * | 4/2003 | Breimer et al. | 514/414 |
| 2002/0137901 A1 | 9/2002 | Cavanaugh | |
| 2004/0204339 A1 * | 10/2004 | DiMartino | 514/2 |

FOREIGN PATENT DOCUMENTS

| | | |
|---|---|---|
| WO | 9810794 A2 | 3/1998 |
| WO | 0033884 A1 | 6/2000 |
| WO | 0061190 A1 | 10/2000 |
| WO | WO 00/66090 A1 | 11/2000 |
| WO | WO 02/00170 A2 | 1/2002 |
| WO | 02091991 A1 | 11/2002 |
| WO | 02094271 A1 | 11/2002 |
| WO | WO 02/091991 A2 | 11/2002 |
| WO | WO 02/091992 A1 | 11/2002 |
| WO | WO 02/092116 A1 | 11/2002 |
| WO | WO 03/004559 A1 | 1/2003 |
| WO | WO 03/032899 A2 | 4/2003 |

OTHER PUBLICATIONS

Weinberg, Iron Withholding: a defense against viral infections, 1996, BioMetals, vol. 9, pp. 393-399.*
Barabas et al., Transferrin Conjugates of Adriamycin are Cytotoxic without Intercalating Nuclear DNA, 1992, Journal of Biological Chemistry, vol. 267, No. 13, pp. 9437-9442.*
Berczi et al., Adriamycin Conjugates of Human Transferrin Bind Transferrin Receptors and Kill K562 and HL60 Cells, 1993, Archives of Biochemistry and Biophysics, vol. 300, No. 1, pp. 356-363.*
Prajapati et al., The search for potent, small molecule NNRTIs: A review, 2009, Bioorganic and Medicinal Chemistry, vol. 17, pp. 5744-5762.*
WHO Global Alert and Response, Hepatitis B, accession online at <<http://www.who.int/csr/disease/hepatitis/whocdscsrlyo20022/en/index2.html on May 4, 2011.*
Vocero-Akbani et al., Killing HIV-infected cells by transduction with an HIV protease-activated caspase-3 protein, 1999, Nature Medicine, vol. 5, No. 1. pp. 29-33.*
Muta et al., Erythroblast transferrin receptors and transferrin kinetics in iron deficiency and various anemias, American Journal of Hematology, 1987, vol. 25, No. 2, abstract.*
Vidal et al., Human T Lymphotropic Virus I Infection Deregulates Surface Expression of the Transferrin Receptor, 1988, Journal of Immunology, vol. 141, No. 3, pp. 984-988.*
Lopez-Guerrero et al., Mechanism of Recognition of Herpes Simplex Virus Type 1-infected Cells by Natural Killer Cells, 1988, Journal of General Virology, vol. 69, pp. 2859-2868.*
All et al., "Transferrin Trojan Horses as a Rational Approach for the Biological Delivery of Therapeutic Peptide Domains," The Journal of Biological Chemistry, 274:34 (1999) pp. 24066-24073.
Bergamini et al., "Selective Inhibition of HIV Replication by Adriamycin in Macrophages but not in Lymphocytes," AIDS Research and Human Retroviruses, 8:7 (1992) pp. 1239-1247.
Kratz et al., "Transferrin Conjugates of Doxorubicin: Synthesis, Characterization, Cellular Uptake, and in Vitro Efficacy," Journal of Pharmaceutical Sciences, American Pharmaceutical Association, 87:3 (Mar. 1, 1998) pp. 338-346.

(Continued)

Primary Examiner — Benjamin P Blumel
(74) Attorney, Agent, or Firm — Rothwell, Figg, Ernst & Manbeck, P.C.

(57) ABSTRACT

Conjugates of transferrin or transcobalamin with anti-viral agents are useful in the treatment of viral infections. Suitable anti-viral agents include apoptosis inducing compounds, compounds which inhibit the replication of the virus, a cytotoxic antibiotic, an alkylating agent, a plant toxin, and a bacterial mutant toxin. Transferrin or transcobalamin is preferably coupled to the anti-viral agent by means of glutaraldehyde.

8 Claims, 3 Drawing Sheets

OTHER PUBLICATIONS

Roy et al., "Infection of Human Monocytes/Macrophages by HIV-1: Effect on Secretion of IL-1 Activity," Immunology, 64 (1988) pp. 233-239.

Hamblin et al., "Photosensitizer Targeting in Photodynamic Therapy. I.Conjugates of Haematoporphyrin With Albumin and Transferrin," J. of Photochemistry and Photobiology B: Biology, 26 (1994) pp. 45-56.

Database CA 'Online!, Chemical Abstracts Service, "Trials of molecular targeting to overcome multidrug resistance". Database accession No. 2000:151715, abstract.

Berczi et al., "Adriamycin conjugates of human transferrin bind transferrin receptors and kill K562 and HL60 cells", Archives of Biochemistry and Biophysics, 300(1), 356-63 CODEN: ABBIA4: ISSN: 003-9861, 1993.

Hoshino et al., "Receptor-binding, in vitro cytotoxicity, and in vivo distribution of transferrin-bound cis-platinum (II) of differing molar ratios", Journal of Controlled Release, vol. 37, No. 1, Nov. 1995, pp. 75-81.

Faulk WP and Johnson PM. Immunological studies of human placentae. Identification and distribution of proteins in mature chorionic villi. Clin Exp Immunol 1977; 27: 365-375.

Faulk WP, Johnson PM, Dorling J and Temple A. Non-specific factors of resistance in human placentae. Prot Biol Fluids 1976; 24: 139-142.

Johnson PM and Faulk WP. Immunological studies of human placentae: Identification and distribution of proteins in immature chorionic villi. Immunology 1978; 34: 1027-1035.

Faulk WP and Galbraith GMP. Trophoblast transferrin and transferrin receptors in the host-parasite relationship of human pregnancy. Proc R Soc Lond B 1979; 204: 83-97.

Hsi BL, Yeh CJG and Faulk WP. Human Amniochorion: Tissue-specific markers, transferrin receptors and histocompatibility antigens. Placenta 1982; 3: 1-12.

Yeh CJG, Hsi BL and Faulk WP. Histocompatibility antigens, transferrin receptors and extra-embryonic markers of human amniotic epithelial cells in vitro. Placenta 1983; 4: 361-368.

Galbraith GMP, Galbraith RM, and Faulk WP. Transferrin binding by human lymphoblastoid cell lines and other transformed cells. Cell Immunology 1980; 49: 215-222.

Faulk, WP, Hsi BL and Stevens PJ. Transferrin and transferrin receptors in carcinoma of the breast. Lancet 1980; ii: 390-392.

Yeh CJG, Taylor C and Faulk WP. Transferrin binding by peripheral blood mononuclear cells in human lymphomas, myelomas and leukemias. Vox Sanguinis 1984; 46: 217-223.

Faulk WP, Harats H and Berczi A. Transferrin receptor growth control in normal and abnormal cells. In: *Oxidoreduction at the Plasma Membrane*. vol. 1. (eds., FL Crane, JD Morre and H Low) CRC Press, Boca Raton, FL, 1990; pp. 205-224.

Yang DC, Wang F, Elliott RL and Head JF. Expression of transferrin receptor and ferritin H-chain mRNA are associated with clinical and histopathological prognostic indicators in breast cancer. Anticancer Res 2001; 21: 541-549.

Barnett D, Wilson GA, Lawrence AC and Buckley GA. Transferrin receptor expression in the leukaemias and lymphoproliferative disorders. Clin Lab Haematol 1987; 9: 361-70.

Whitney JF, Clark JM, Griffin TW, Gautam S and Leslie KO. Transferrin receptor expression in nonsmall cell lung cancer. Histopathologic and clinical correlates, Cancer 1995; 76: 20-25.

Recht L, Torres CO, Smith TW, Raso V and Griffin TW. Transferrin receptor in normal and neoplastic brain tissue: implications for brain-tumor immunotherapy. J Neurosurg 1990; 72: 941-945.

Sciot R, Paterson AC, van Eyken P, Callea F, Kew MC and Desinet VJ. Transferrin receptor expression in human hepatocellular carcinoma: an immunohistochemical study of 34 cases. Histopathol 1988; 12: 53-63.

Seymour GJ, Walsh MD, Lavin MF, Strutton G and Gardiner RA. Transferrin receptor expression by human bladder transitional cell carcinomas. Urol Res 1987; 15: 341-344.

Lindholm ML, Lindberg, LA, Vilja P, Puolakka VM, Nordling S, Schroder T and Schroder J. Expression of the human transferrin receptor in subrenal capsule assay in the mouse. J Surg Oncol 1988; 38: 57-62.

Hereiz HA and Bayoumi FA. Evaluation of diagnosis of ovarian malignancy using immunohistochemical technique. J Egyptian Public Hlth Assoc 1992; 67: 697-707.

Mederios LJ, Picker LJ, Horning SJ and Warnke RA. Transferrin receptor expression by non-Hodgkin's lymphomas. Correlation with morphologic grade and survival. Cancer 1988; 61: 1844-1851.

Soyer HP, Smolle J, Torne R and Kerl H. Transferrin receptor expression in normal skin and in various cutaneous tumors. J Cutaneous Pathol 1987; 14: 1-5.

Lesley J, Hyman R, Schulte R and Trotter J. Expression of transferrin receptor on murine hematopoietic progenitors. Cell Immunol 1984; 83: 14-25.

Testa U, Pelosi E and Peschle C. The transferrin receptor, Crit Rev Oncogen 1993; 4: 241-276.

Bothwell TA, Charlton RW, Cook JD and Finch CA. *Iron Metabolism in Man*, Blackwell Scientific, Oxford, 1979.

Ponka P and Lok CN. The transferrin receptor: role in health and disease. Int J Biochem Cell Biol 1999; 31: 1111-1137.

Hamilton TA, Gray PW and Adams DO. Expression of the transferrin receptor on murine peritoneal macrophages is modulated by in vitro treatment with interferon gamma. Cell Immunol 1984; 89: 478-488.

Byrd TF and Horowitz MA. Interferon gamma-activated human monocytes downregulate transferrin receptors and inhibits the intracellular multiplication of *Legionella pneumophila* by limiting the availability of iron. J Clin Invest 1989; 83: 1457-1465.

Kronke M, Leonard W, Depper JM and Greene WC. Sequential expression of genes involved in human T lymphocyte growth and differentiation. J Exp Med 1985; 161: 1593-1598.

Galbraith RM and Galbraith GM. Expression of transferrin receptors on mitogen-stimulated human peripheral blood lymphocytes: relation to cellular activation and related metabolic events. Immunology 1983; 133: 703-710.

Neckers LM and Cossman J. Transferrin receptor induction in mitogen-stimulated human T lymphocytes is required for DNA synthesis and cell division and is regulated by interleukin 2. Proc Nat Acad Sci USA 1983; 80: 3494-3498.

Testa U, Kuhn L, Petrini M, Quaranta MT, Pelosi E and Peschle C. Differential regulation of iron regulatory element-binding protein(s) in cell extracts of activated lymphocytes versus monocytes-macrophages. J Biol Chem 1991; 266: 3925-3930.

Seiser C, Texieira S and Kuhn LC. Interleukin-2-dependent transcriptional and post-transcriptional regulation of transferrin receptor mRNA. J Biol Chem 1993; 268: 13,074-13,080.

Neckers LM, Yenokida G and James SP. The role of the transferrin receptor in human B lymphocyte activation. J Immunol 1984; 133: 2437-2441.

Neckers LM and Trepel JB. Transferrin receptor expression and the control of cell growth. Cancer Invest 1986; 4: 461-470.

Yeh CJG, Papamichail M and Faulk WP. Loss of transferrin receptors following induced differentiation of LH-60 promyelocytic leukemia cells. Exper Cell Res 1982; 138: 439-431.

Barker KA and Newburger PE. Relationships between the cell cycle and the expression c-myc and transferrin reeptor genes during induced myeloid differentiation. Exper Cell Res 1990; 186: 1-5.

Klausner RD, Rouault TA and Harford JB. Regulating the fate of mRNA: the control of cellular iron metabolism. Cell 1993; 72: 19-28.

Haile DJ. Regulation of genes of iron metabolism by the iron-response proteins. Am J Med Sciences 1999; 318: 230-240.

Gatter KC, Brown G, Trowbridge IS, Woolston RE and Mason DY. Transferrin receptors in human tissues: their distribution and possible clinical relevance. J Clin Pathol 1983; 36: 539-545.

Faulk WP and Hunt JS. Human placentae: view from an immunological bias. Am J Reprod Immunol 1990; 21: 108-113.

Broadwell RD, Baker-Caims BJ, Friden PM, Oliver C and Villegas JC. Transcytosis of protein through the mammalian cerebral epithelium and endothelium. III. Receptor mediated transcytosis through the blood-brain barrier of blood-borne transferrin and antibody against transferrin receptor. Exp Neurol 1996; 142: 47-65.

Ponka P, Beaumont C and Richardson DR. Function and regulation of transferrin and ferritin. Seminars in Hematol 1998; 35: 35-54.

Sylvester SR and Griswold MD. The testicular iron shuttle: A "nurse" function of the Sartoli cells. J Androl 1994; 15: 381-385.

Yeh CJG and Faulk WP. Killing of human tumor cells in culture with adriamycin conjugates of human transferrin. Clin Immunol Immunopath 1984; 32: 1-11.

Yeh CJG, Taylor CG and Faulk WP. Targeting of cytotoxic drugs by transferrin receptors: Selective killing of acute myelogenous leukemia cells. Protides Biol Fluids 1984; 32: 441-444.

Berczi A, Barabas K, Sizensky JA and Faulk WP. Adriamycin conjugates of human transferrin bind transferrin receptors and kill K562 and HL60 cells. Arch Biochem Biophys 1993; 300: 356-363.

Lai BT, Gao JP and Lanka KW. Mechanism of action and spectrum of cell lines sensitive to a doxorubicin-transferrin conjugate. Cancer Chemother & Pharmacol 1998; 41: 155-160.

Kratz F, Beyer U, Roth T, Tarasova N, Collery P, Lechenault F, Cazabat A, Schumacher P, Unger C and Falken U. Transferrin conjugates of doxorubicin: synthesis, characterization, cellular uptake, and in vitro efficacy. J Pharm Sciences 1998; 87: 338-346.

Tanaka T, Kaneo Y and Miyashita M. Synthesis of transferrin-mitomycin C conjugate as a receptor-mediated drug targeting system. Biol Pharm Bull 1996; 19: 774-777.

Sasaki K, Kohgo Y, Kato J, Kondo H and Niitsu Y. Intracellular metabolism and cytotoxicity of transferrin-neocarzinostatin conjugates of differing molar ratios. Jpn J Cancer Res 1993; 84: 191-196.

Laske DW, Youle RJ and Oldfield EH. Tumor regression with regional distribution of the targeted toxin TF-CRM107 in patients with malignant brain tumors. Nature Med 1997; 3: 1362-1368.

Beyer U, Roth T, Schumacher P, Maier G, Unold A, Frahm AW, Fiebig HH, Unger C and Kratz F. Synthesis and in vitro efficacy of transferrin conjugates of the anticancer drug chlorambucil. J Med Chem 1998; 41: 2701-2708.

Bicamumpaka E and Page M. In vitro cytotoxicity of paclitaxel-transferrin conjugate on H69 cells. Oncol Reports 1998; 5: 1381-1383.

Lemieux P, Page M and Noel C. In vivo cytotoxicity and antineoplastic activity of a transferrin-daunorubicin conjugate. In Vivo 1992; 6: 621-627.

Guo M, Sun H, McArdle HJ, Gambling L and Sadler PJ. Ti(IV) uptake and release by human serum transferrin and recognition of Ti(IV)-transferrin by cancer cells: understanding the mechanism of action fo the anticancer drug titanocene dichloride. Biochem 2000; 39: 10023-10033.

Shah D and Shen WC. Transcellular delivery of an insulin-transferrin conjugate in enterocyte-like Caco-2 cells. J Pharm Sciences 1996; 85: 1306-1311.

Drobyski WR, Ul-Haq R, Majewski D and Chitambar CR. Modulation of in vitro and in vivo T-cell responses by transferrin-gallium and gallium nitrate. Blood 1996; 88: 3056-3064.

Hoshino T, Misaki M, Yamamoto M, Shimizu H, Ogawa Y and Toguchi H. In vitro cytotoxicities and in vivo distribution of transferrin-platinum(II) complex. J Pharm Sciences 1995; 84: 216-221.

Ippoliti R, Ginobbi P, Lendaro E, D'Agostino I, Ombres D, Benedetti PA, Brunori M and Citro G. The effect of monensin and chloroquine on the endocytosis and toxicity of chioneric toxins. Cell Mol Life Sci 1998; 54: 866-875.n Kratz F, Hartmann F, Keppler B and Messor L. The binding properties of two antitumor ruthenium(III) complexes to apotransferrin. J Biol Chem 1994; 269: 2581-2588.

Park E, Starzyk RM, McGrath JP, Lee T, George J, Schultz AJ, Lynch P and Putney SD. Production and characterization of fusion proteins containing transferrin and nerve growth factor. J Drug Targeting 1998; 6: 53-64.

Ali SA, Joao HC, Hammerschmid F, Eder J and Steinkasserer A. Transferrin Trojan Horses as a rational approach for biological delivery of therapeutic peptide domains. J Biol Chem 1999; 274: 24066-24073.

Peter, K and Richards FM. Chemical cross-linking: reagents and problems in studies of membrane structure. Annu Rev Biochem 1977; 46: 523-551.

Rhodes J. Evidence for an intercellular covalent reaction essential in antigen-specific T cell activation. J Immunol 1989; 143: 1482-1489.

Greenfield RS, Kaneko T, Daues A, Edson MA, Fitzgerald KA, Olech LJ, Grattan JA, Spitalny GL and Braslawsky GR. Evaluation in vitro of adriamycin immunoconjugates synthesized using an acid-sensitive hydrazone bond. Cancer Res 1990; 50: 6600-6607.

Braslawsky GR, Edson MA, Pearce W, Kaneko T and Greenfield RS. Antitumor activity of adriamycin (hydrazone-linked) immunoconjugates compared with free adriamycin and specificity of tumor cell killing. Cancer Res 1990; 50: 6608-6614.

O'Keefe DO and Draper RK. Characterization of transferrin-diphtheria toxin conjugate. J Biol Chem 1985; 260: 932-937.

Neidle S, Pearl LH and Skelly JV. DNA structure and perturbation by drug binding. Biochem J 1987; 243: 1-13.

Tritton TR. Cell surface actions of adriamycin. Pharmacol & Therapeutics 1991: 49: 293-309.

Maestre N, Tritton TR, Laurent G and Jaffrezou JP. Cell surface-directed interaction of anthramyclines leads to cytotoxicity and nuclear factor kappaB activation but not apoptosis signaling. Cancer Res 2001; 61: 2558-2561.

Fong WF, Lam W, Yang M and Wong JT-F. Partial synergism between dextran-conjugated doxorubicin and cancer drugs on the killing of multidrug resistant KB-VI cells. Anticancer Res 1996; 16: 3773-3778.

Barabas K, Sizensky JA and Faulk WP. Transferrin conjugates of adriamycin are cytotoxic without intercalating nuclear DNA. J Biol Chem 1992; 267: 9437-9442.

Faulk WP, Barabas K, Sun IL and Crane FL. Transferrin-adriamycin conjugates which inhibit tumor cell proliferation without interaction with DNA inhibit plasma membrane oxidoreductase and proton release in K562 cells. Biochem Int 1991; 25: 815-822.

Berczi A, Ruthner M, Szuts V, Fritzer M, Schweinzer E and Goldenberg H. Influence of conjugation of doxorubicin to transferrin on the iron uptake by K562 cells via receptor-mediated endocytosis. Euro J Biochem 1993; 213: 427-436.

Barabas K, Sizensky J and Faulk WP. Evidence in support of the plasma membrane as the target for transferrin-adriamycin conjugates in K562 cells. Am J Reprod Immunol 1991; 25: 120-124.

Szuts V, Berczi A, Schweinzer E and Goldenberg H. Binding of doxorubicin-conjugated transferrin to U937 cells. J Receptor Res 1993; 13: 1041-1054.

Ruthner M, Berczi A and Goldenberg H. Interaction of a doxorubicin-transferrin conjugate with isolated transferrin receptors. Life Sci 1994; 54: 35-40.

Sainte-Marie I, Lafont V, Pecheur EI, Favero J, Philippot JR and Bienvenue A. Transferrin receptor functions as a signal-transduction molecule for its own recycling via increases in the internal Ca++ concentration. Euro J Biochem 1997; 250: 689-697.

Klausner RD, vanReuswoude J, Ashwell G, Kempf C, Schechter AN, Dean A and Bridges K. Receptor-mediated endocytosis of transferrin in K562 cells. J Biol Chem 1983; 258: 4715-4724.

Richardson DR and Ponka P. The molecular mechanisms of a metabolism and transport of iron in normal and neoplastic cells. Biochim Biophy Acta 1997; 1331: 1-40.

Baker MA and Lawen A. Plasma membrane NADH-oxidase system: a critical review of the structural and functional data. Antioxidants & Redox Signaling 2000; 2: 197-212.

Sun IL, Navas P, Crane FL, Morre DJ and Low H. NADH-diferric transferrin reductase in liver plasma membranes. J Biol Chem 1987; 262: 15915-15921.

Sun IL, Navas P, Crane FL, Morre DJ and Low H. Diferric transferrin reductase in the plasma membrane is inhibited by adriamycin. Biochem Int 1987; 14: 119-127.

Faulk WP, Harats H, McIntyre JA, Berczi A, Sun IL and Crane FL. Recent advances in cancer research: Drug targeting without the use of Monoclonal antibodies Am J Reprod Immunol 1989; 21: 151-154.

Morre DJ, Kim C, Paulik M, Morre DM and Faulk WP. Is the drug-response NADH-oxidase of the cancer cell plasma membrane a molecular target for adriamycin? Bioenerg Biomembr 1997; 29: 269-280.

Sun IL, Sun EE, Crane FL, Morre DJ and Faulk WP. Inhibition of transplasma membrane electron transport by transferrin-adriamycin conjugates. Biochim Biophy Acta 1992; 1105: 84-88.

Crane FL, Low H, Sun IL, Morre DJ and Faulk WP. Interaction between oxidoreductase, transferrin receptor and channels in the plasma membrane. In: *Growth Factors from Genes to Clinical Applications* (eds, VR Sara, K Hall and H Low) Raven Press, New York, 1990; pp. 228-239.

Hileti D, Panayiotidis P and Hoffbrand V. Iron chelators induce apoptosis in proliferating cells. Brit J Haematol 1995; 89: 181-187.

Leardi A, Caraglia M, Selleri C, Pepe S, Pizzi C, Notaro R, Fabbrocini A, De Lorenzo S Musico M, Abbruzzese A, Bianco A and Tagliaferri P. Desferioxamine increases iron depletion and apoptosis induced by ara-C of human myeloid leukemic cells. Brit J Haematol 1998; 102: 746-752.

Barabas K, Miller SJ and Faulk WP. Regulation of transferrin receptor mRNA stability in drug-sensitive and drug-resistant cancer cells. To be submitted for publication, 2003.

Hentze MW and Kuhn LC. Molecular control of vertebrate iron-metabolism mRNA-based regulatory circuits operated by iron, nitric and oxidative stress. Proc Natl Acad Sci USA 1996; 93: 8175-8182.

Pantapoulos K and Hentze MW. Rapid responses to oxidative stress mediated by iron regulatory protein. EMBO J 1995; 14: 2917-1924.

Wardrop SL, Watts RN and Richardson DR. Nitrogen monoxide activates iron regulatory protein 1 RNA-binding activity by two possible mechanisms: effect on the 4Fe-4S cluster and iron mobilization from cells. Biochemistry 2000; 39: 2748-2758.

Eisenstein RS. Iron regulatory proteins and the molecular control of mammalian iron metabolism. Annu Rev Nutr 2000; 20: 627-662.

Richardson DR, Naumannova V, Nagy E and Ponka P. The effect of redox-related species of nitrogen monoxide on transferrin and iron uptake and cellular proliferation of erythroleukemia (K562) cells. Blood 1995; 86: 3211-3219.

Kim S and Ponka P. Effects of interferon-gamma and lipopolysaccharide on macrophage iron metabolism are mediated nitric oxide-induced degradation of iron regulatory protein 2. J Biol Chem 2000; 275: 6220-6226.

Nestel FP, Green RN, Kickian K, Ponka P and Lapp WS. Activation of macrophage cytostatic effector mechanisms during acute graft-versus-host disease: release of intracellular iron and nitric oxide-mediated cytostasis. Blood 2000; 96: 1836-1843.

Kim S and Ponka P. Control of transferrin receptor expression via nitric oxide-mediated modulation of iron-regulatory protein 2. J Biol Chem 1999; 274: 33035-33042.

Laske DW, Ilercil O, Akbasak A, Youle RJ and Oldfield EH. Efficacy of direct intratumoral therapy with targeted protein toxins for solid human gliomas in nude mice. J Neurosurg 1994; 80: 520-526.

Singh M, Atwal H and Micetich R. Transferrin directed delivery of adriamycin to human cells. Anticancer Res 1998; 18(3A): 1423-1427.

Sato Y, Yamauchi N, Takahashi M, Sasaki K, Fukaura J, Neda H, Fujii S, Hirayma M, Itoh Y, Koshita Y, Kogawa K, Kato J, Sakamaki S and Niitsu Y. In vivo gene delivery to tumor cells by transferrin-streptavidin-DNA conjugate. FASEB Journal 2000; 14: 2108-2118.

Oldfield EH and Youle RJ. Immunotoxins for brain tumor therapy. Cur Top Microbiol Immunol 1998; 234: 97-114.

Kohgo Y, Kato J, Sasaki K and Kondo H. Targeting chemotherapy with transferrin-neocarzinostatin. Japanese J Cancer Chemotherapy 1988; 15: 1072-1076.

Faulk WP, Taylor CG, Yeh G and McIntyre JA. Preliminary clinical study of transferrin-adriamycin conjugate for drug delivery to acute leukemia patients. Mol Biother 1990; 2: 57-60.

Laske DW, Morrison PF, Lieberman DM Carthesy ME, Reynolds JC, Stewart-Henney PA, Koong SS, Cummins A, Paik CH and Oldfield EH. Chronic interstitial infusion of protein to primate brain: determination of drug distribution and clearance with single-photon emission computerized tomography imaging. J Neurosurg 1997; 87: 586-594.

Marbeuf-Gueye C, Ettori D, Priebe W, Kozlowski H and Garnier-Suillerot A. Correlation between the kinetics of athracycline uptake and the resistance factor in cancer cells expressing the multidrug resistance protein or the P-glycoprotein. Biochem Biophy Acta 1999; 1450: 374-384.

Fritzer M, Barabas K, Szuts V, Berczi A, Szekeres T, Faulk WP and Goldenberg H. Cytotoxicity of a transferrin-adriamycin conjugate to anthracyloine resistant cells. Int J Cancer 1992; 52: 619-623.

Hatano T, Ohkawa K and Matsuda M. Cytotoxic effect of the protein-doxorubicin conjugates on the multidrug-resistant human myelogenous leukemia cell line, K562, in vitro. Tumor Biology 1993; 14: 288-294.

Lemieux P and Page M. Sensitivity of multidrug-resistant MCF-7 cells to a transferrin-doxorubicin conjugate. Anticancer Res 1994; 14(2A): 397-403.

Fritzer M, Szekeres T, Szuts V, Jraayam HN and Goldenberg H. Cytotoxic effects of a doxorubicin-transferrin conjugate in multidrug-resistant KB cells. Biochem Pharm 1996; 51: 489-493.

Wang F, Jiang X, Yang DC, Elliot RL and Head JF. Doxorubicin-gallium-transferrin conjugat overcomes multidrug resistance: evidence for drug accumulation in the nucleus of drug resistant MCF-7/ADR cells. Anticancer Res 2000; 20: 799-808.

Soma CE, Dubernet C and Barratt G. Ability of doxorubicin-loaded nanoparticles to overcome multidrug resistance of tumor cells after their capture by macrophages. Pharm Res 1999; 16: 1710-1716.

Mazel M, Clair P, Rousselle C, Vidal P, Scherrmann J-M, Mathieu D and Temsamani J. Doxorubicin-peptide conjugates overcome multidrug resistance. Anti-Cancer Drugs 2001; 12: 107-116.

Anderson BF, Baker HM, Norris GE, Rumball SV and Baker EN. Apolactoferrin structure demonstrates ligand-induced conformational change in transferrins. Nature 1990; 344: 784-787.

Baker EN. Structure and reactivity of transferrin. Adv Inorg Chem 1994; 41: 389-463.

Harris WR. Equilibrium constants for the complexation of metal ions by serum transferrin. Adv Exp Med & Biol 1989; 249: 67-93.

Li H, Sadler PJ and Sun H. Unexpectedly strong binding of a large metal ion ($Bi^{3+}$) to human serum transferrin. J Biol Chem 1996; 271: 9483-8489.

Battistuzzi G, Calzolai L, Messori L and Sola M. Metal-induced conformational heterogeneity of transferrins: a spectroscopic study of indium (III) and other metals (III)-substituted transferrins. Biochem Biophys Res Com 1995; 206: 161-170.

Kubal G, Mason AB, Patl SU, Sadler PJ and Woodworth RC. Oxalate- and $Ga^{3+}$-induced structural changes in human transferrin and its recombinant N-lobe, $^1$H NMR detection of preferential C-lobe $Ga^{3+}$ binding. Biochem 1993; 32: 3387-3395.

Grossman JG, Neu M, Evans RW, Lindley PF, Appel H and Hasnain SS. Metal-induced conformational changes in transferrins. J Mol Biol 1993; 229: 585-590.

Sun H, Li H, Mason AB, Woodworth RC and Sadler PJ. N-lobe versus C-lobe complexation of bismuth by human transferrin. Biochem J 1999; 337: 105-111.

Dobson CB, Graham J and Itzhaki RF. Mechanism of uptake of gallium by human neuroblastoma cells and effects of gallium and aluminum on cell growth, lysosomal protease, and choline acetyl transferase activity. Exp Neurol 1998; 153: 342-350.

Abreo K, Jangula J, Jain SK, Sella M and Glass J. Aluminum uptake and toxicity in cultured mouse hepatocytes. J Am Soc Nephrol 1991; 1: 1299-1304.

Sun H, Li H, Mason AB, Woodworth RC Sadler PJ. Competitive binding of bismuth to transferrin and albumin in aqueous solution and in blood plasma. J Biol Chem 2001; 276: 8829-8835.

Gallori E, Vettori C, Alessio E, Vilchez FG, Vilaplana R, Orioli P, Casini A and Messori L. DNA as a possible target for antitumor ruthenium complexes. Arch Biochem Biophy 2000; 376: 156-162.

Ward SG and Taylor RC. In, Metal-Based Anti-Tumor Drugs (Gielen MF, Ed) 1988, pp. 1-54, Fruend Publishing House Ltd., London.

Kubal G and Sadler PJ. Sequential binding of aluminum (3+) to the C- and N-lobe of human serum transferrin detected by $^1$H NMR spectroscopy. J Am Chem Soc 1992; 114: 1117-1118.

Kubal G, Mason AB, Sadler PJ, Tucker A and Woodworth RC. Uptake of $Al^{3+}$ into the N-lobe of human serum transferrin, Biochem J 1992; 285: 711-714.

Van Rensburg SJ, Carstens ME, Potocnik FCV and Taljaard JJF. The effect of iron and aluminum on transferrin and other serum proteins as revealed by isoelectric focusing gel electrophoresis. Annals NY Acad Sci 2000; 903: 150-155.

Kratz F, Hartmann M, Keppler B and Messori L. The binding properties of two antitumor ruthenium (III) complexes to apotransferrin. J Biol Chem 1994; 269: 2581-2588.

Guo M, Sun H, McArdle JH, Gambling L and Sadler PJ. $Ti^{IV}$ uptake and release by human serum transferrin and recognition of $Ti^{IV}$-transferrin by cancer cells: understanding the mechanism of action of the anticancer drug titanocene dichloride. Biochem 2000; 39: 10023-10033.

Roskams AJ and Cosmor JR. Aluminum access to the brain: a role for transferrin and its receptor. Proc Natl Acad Sci USA 1990; 87: 9024-9027.

Knorr GM and Chitamber CR. Gallium-pyridoxal isonicotinoyl hydrazone (Ga-PIH), a novel cytotoxic gallium complex. A comparative study with gallium nitrate. Anticancer Res 1998; 18 (3A): 1733-1737.

Kasai K. Hori MT and Goodman WG. Transferrin enhances the antiproliferative effect of aluminum on osteoblast-like cells. Am J Physiol 1991; 260 (4Pt1): E537-543.

McGregor SJ, Naves ML, Birly AK, Russell NH, Halls D, Junor BJ and Brock JH. Interaction of aluminum and gallium with human lymphocytes: the role of transferrin. Biochim Biophys Acta 1991; 1095: 196-200.

Abreo K and Glass J. Cellular, biochemical, and molecular mechanisms of aluminium toxicity. Nephrol Dial Transplant 1993; 8 Suppl 1: 5-11.

Kratz F, Mulinacci N, Messori L, Bertini I and Keppler BK. In, Metal Ions in Biology and Medicine, vol. 2, pp. 69-74, John Libbey Limited Eurotext, Paris.

WiSniewski MZ, Wietrzyk J and Opolski A. Novel Ru(III), Rh(III), Pd(II) and Pt(II) complexes with ligands incorporating azole and pyrimidine rings. I. Antiprolifeartive activity in vitro. Arch Immunolog Therap Exper 2000; 48: 51-55.

Frasca DR, Gehrig LE and Clarke MJ. Cellular effects of transferrin coordinated to J Inorg Biochem 2001; 83: 139-149.

Whelan HR, Williams MB, Bijic DM, Flores RE, Schmidt MH, McAuliffe TL and Chitambar CR. Gallium nitrate delays the progression of microscopic disease in a human medulloblastoma murine model. Ped Neurol 1994; 11: 44-46.

Ganot PO. Metabolism and possible health effects of aluminum. Envir Hlth Perspect 1986; 65: 363-441.

Keppler BK, Berger MR, and Heim ME. New tumor-inhibiting metal complexes. Cancer Treat Rev 1990; 17: 261-277.

Seelig MH, Berger MR and Keppler BK. Antineoplastic activity of three ruthenium derivatives against chemically induced colorectal carcinoma in rats; J Cancer Res Clin Oncol 1992; 188: 195-200.

Webster LK, Olver IN, Stokes KH, Sephton RG, Hillcoat BL and Bishop JF, A pharmacokinetic and phase II study of gallium nitrate in patients with non-small cell lung cancer. Cancer Chemother & Pharmacol 2000; 4S: 55-58.

Brechbiel MW. Chelated metal ions for therapeutic and diagnostic applications. Exper Biol & Med 2001; 226: 627-628.

Veronese I, Giussani A, Cantono MC, de Bartolo D, Roth P and Werner E. Kinetics of systemic ruthenium in human blood using a stable tracer. J Radiol Protect 2001; 21: 31-38.

Crul M, van den Bongard HJ, Tibben MM, van Tellingen O, Sava G, Schellens JH and Beijnen JH. Validated method for the determination of the novel organo-ruthenium anticancer drug NAMI-A in human biological fluids, by Zeeman atomic absorptiono spectrometry. Fresenius J Anal Chem 2001; 369: 442-445.

Howard JB and Rees DC. Perspectives on non-heme iron protein chemistry. Adv Protein Chem 1991; 42: 199-280.

Barabas K and Faulk WP: Transferrin receptors associate with drug resistance in cancer cells. Biochem Biophys Res Com 1993; 197: 702-708.

Luttropp CA, Jackson JA, Jones BJ, Sohn MH, Lynch RE and Morton KA. Uptake of Gallium-67 in transfected cells on tumors absent or enriched in the transferrin receptors. J Nucl Med 1998; 39: 1405-1411.

Pannccio M, Zalcberg JR, Thompson CH, Leyden JM, SullivanJR, Lichtenstein M and McKenzie IF. Heterogeneity of the human transferrin receptor and use of anti-transferrin receptor antibodies to detect tumors in vivo. Immunol & Cell Biol 1987; 65: 461-472.

Farley J, Loup D, Nelson M, Miller MJ, Taylor R and Gray K. Transferrin in normal and neoplastic endocervical tissues: distribution and receptor expression. Analyst & Quant Cytol & Histol 1998; 20: 238-249.

Sausville EA and Feigal E. Evolving approaches to cancer drug discovery and development at the National Cancer Institute, USA, Annals Oncol 1999; 10: 1287-1291.

Surolia N and Misquith S. Cell surface directed targeting of toxin to human malaria parasite. FEBS Lett 1996; 396:57-61.

Ohno H, Aguilar RC, Fournier M-C, Hennecke S, Cosson P and Boifacirio JS. Interaction of endocytic signals from the HIV-1 envelope glycoprotein complex with members of the adaptor medium chain family. Virology 1997; 238: 305-315.

Woodward JE, Bayer AL and Baliga P. Enhanced allograft survival via simultaneous blockade of transferrin receptor and interleukin-2-receptor. Transplantation 1999; 68: 1369-1376.

Som P, Oster ZH, Matsui K, Guglielmi G, Persson BR, Pellettieri ML, Srivastrava SC, Richards P, Atkins HL and Brill AB. 97Ru-transferrin uptake in tumor and abscess. Eur J Nucl Med 1983; 8: 491-494.

Lambert JR. Pharmacology of bismuth-containing compounds. Rev Inf Dis 1991; 13(Suppl 8): S691-S695.

Pariente JL, Bordenave L, Bareille R, Ohayon-Courtes C, Baquey C and LeGuillou M. In vitro cytocompatibility of radio-opacifiers used in ureteral endoprosthesis; Biomaterials 1999; 20: 523-527.

Krari N, Mauras Y and Allain P. Enhancement of bismuth toxicity by L-cysteine. Res Com Mol Pathol & Pharmacol 1995; 89: 357-364.

Stoltenberg M, Schionning S and Danscher G. Retrograde axonal transport of bismuth: an autometrallographic study. Acta Neuropathol 2001; 101: 123-128.

* cited by examiner

Figure 1. Dose-Response Curve against HIV-1

Figure 2. Dose Response-Curve of against HBV

Figure 3. Dose-Response Curve against CMV

TARGETED DELIVERY OF DRUGS FOR THE TREATMENT OF VIRAL INFECTIONS

CROSS REFERENCE TO RELATED APPLICATION

This application is a continuation of U.S. application Ser. No. 10/477,997, filed Nov. 17, 2003, which is a 35 USC § 371 National Phase Entry Application from PCT/US02/11892, filed May 15, 2002, and designating the U.S, which claims priority benefit of U.S. Provisional Application Nos. 60/290,668 filed May 15, 2001 and 60/355,394 filed Feb. 8, 2002, disclosure of which are hereby incorporated by reference.

FIELD OF THE INVENTION

This invention relates generally to the field of bioaffecting materials and, more specifically to bioaffecting materials suitable for treating cells, including human cells, that are stressed, especially those stressed as a result of a viral infection.

BACKGROUND OF THE INVENTION

Two common problems in treatments which involve drugs are drug-toxicity, which debilitates patients, and drug-resistance, which requires more drugs and thus amplifies the problem of drug-toxicity, often resulting in death. One way to solve the problem of drug-toxicity is to deliver drugs so they are targeted only to the diseased cells. Many researchers are working to develop antibodies to deliver drugs, and this approach holds promise, but antibodies are not without problems. For example, they often cross-react with normal tissues, and they can damage blood vessels (e.g., vascular leak syndrome) and cause dangerous allergic reactions (e.g. anaphylaxis).

The treatment of malignant cells by the delivery of drugs, including drugs that are toxic to such cells, is not new. U.S. Pat. Nos. 4,886,780; 4,895,714; 5,000,935; and 5,108,987 to Faulk and U.S. Pat. No. 4,590,001 to Stjernholm et. al., describe cytotoxic or radioimaging materials conjugated to proteins, mainly to transferrin, as treatments for cancerous cells or for imaging cancerous cells. These publications disclose useful methods for making and using such materials.

It is known that stressed cells, such as, for example, human cells hosting a viral infection and human cells invaded by cancer, call for an increased delivery of nutrients, such as iron, by presenting an increased number of receptors for nutrient carriers, such as transferrin in the case of iron. The increase in receptors for nutrient carriers in stressed cells is known to be relatively constant and orders of magnitude greater in number than in unstressed cells, which are known to show receptors intermittently and in relatively smaller numbers. The publications listed above, and others, disclose taking advantage of the increased number of receptors, especially for transferrin, presented by cancer containing cells to deliver imaging materials or drugs or both to the stressed cell.

No single study has asked if all stressed cells have up-regulated transferrin receptors, or if all normal cells have down-regulated transferrin receptors, but data from many quarters suggest that all normal cells have down-regulated transferrin receptors. For example, immature erythrocytes (i.e., normoblasts and reticulocytes) have transferrin receptors on their surfaces, but mature erythrocytes do not (Lesley J, Hyman R, Schulte R and Trotter J. Expression of transferrin receptor on murine hematopoietic progenitors. Cell Immunol 1984; 83: 14-25). Circulating monocytes also do not have up-regulated transferrin receptors (Testa U, Pelosi E and Peschle C. The transferrin receptor. Crit Rev Oncogen 1993; 4: 241-276), and macrophages, including Kupffer cells, acquire most of their iron by a transferrin-independent method of erythrophagocytosis (Bothwell T A, Charlton R W, Cook J D and Finch C A. *Iron Metabolism in Man*, Blackwell Scientific, Oxford, 1979). In fact, in vivo studies indicate that virtually no iron enters the reticuloendothelial system from plasma transferrin (for review, see Ponka P and Lok C N. The transferrin receptor: role in health and disease. Int J Biochem Cell Biol 1999; 31: 1111-1137.). Macrophage transferrin receptors are down-regulated by cytokines such as gamma interferon (Hamilton T A, Gray P W and Adams D O. Expression of the transferrin receptor on murine peritoneal macrophages is modulated by in vitro treatment with interferon gamma. Cell Immunol 1984; 89: 478-488.), presumably as a mechanism of iron-restriction to kill intracellular parasites (Byrd T F and Horowitz M A. Interferon gamma-activated human monocytes downregulate transferrin receptors and inhibits the intracellular multiplication of *Legionella. pneumophila* by limiting the availability of iron. J Clin Invest 1989; 83: 1457-1465.).

In resting lymphocytes, not only are transferrin receptors down-regulated, but the gene for the transferrin receptor is not measurable (Kronke M, Leonard W, Depper J M and Greene W C. Sequential expression of genes involved in human T lymphocyte growth and differentiation. J Exp Med 1985; 161: 1593-1598). In contrast, stimulated lymphocytes up-regulate transferrin receptors in late $G_1$ (Galbraith R M and Galbraith G M. Expression of transferrin receptors on mitogen-stimulated human peripheral blood lymphocytes: relation to cellular activation and related metabolic events. Immunology 1983; 133: 703-710). Receptor expression occurs subsequent to expression of the c-myc proto-oncogene and following up-regulation of IL-2 receptor (Neckers L M and Cossman J. Transferrin receptor induction in mitogen-stimulated human T lymphocytes is required for DNA synthesis and cell division and is regulated by interleukin 2. Proc Nat Acad Sci USA 1983; 80: 3494-3498.), and is accompanied by a measurable increase in iron-regulatory protein binding activity (Testa U, Kuhn L, Petrini M, Quaranta M T, Pelosi E and Peschle C. Differential regulation of iron regulatory element-binding protein(s) in cell extracts of activated lymphocytes versus monocytes-macrophages. J Biol Chem 1991; 266: 3925-3930), which stabilizes transferrin receptor mRNA (Seiser C, Texieira S and Kuhn L C. Interleukin-2-dependent transcriptional and post-transcriptional regulation of transferrin receptor mRNA. J Biol Chem 1993; 268: 13,074-13,080.). This is true for both T and B lymphocytes (Neckers L M, Yenokida G and James S P. The role of the transferrin receptor in human B lymphocyte activation. J Immunol 1984; 133: 2437-2441), and is an IL-2-dependent response (Neckers L M and Trepel J B. Transferrin receptor expression and the control of cell growth. Cancer Invest 1986; 4: 461-470).

The best understood material mentioned in the above-listed publications is a conjugate of transferrin and doxorubicin, a well known and effective cytotoxic molecule. Although effective against cancers, doxorubicin has a maximum lifetime dosage for humans due to its cumulative cardiotoxicity. The conjugate has been shown to be effective in surprisingly low doses in killing a variety of types of cancers, including drug-resistant cancers in humans.

Well known and presently used methods for treating serious viral infections, such as infections by the human immunodeficiency virus (HIV) include blocking cell receptors that the virus uses to enter the cell, interfering with fusion mechanisms, and interfering with cell enzymes hijacked by the virus such as proteases and reverse transcriptases. Such methods and the drugs used in the methods, although effective in prolonging the life of seriously ill patients, have not resulted in wholesale cures. The materials themselves are well known to be prohibitively expensive for use in many parts of the world. Often, treatment with such drugs burdens a patient with complex dosing schemes and presents unpleasant side effects.

There is a need for materials for use in the treatment of high profile conditions such as AIDS, caused by HIV infections, that provide more effective results at a lower cost and fewer side effects for patients. There is also a need for materials for use in treating cells infected with a variety of other viral infections that burden societies, such as cytomegalovirus, adenoviruses, hepatitis viruses, herpes simplex viruses, and the like. There is also a need for drugs that kill such viruses and a variety of cancers without the use of cytotoxic materials even in small amounts.

DESCRIPTION OF THE RELATED ART

All drugs currently approved by the FDA for treatment of AIDS patients are designed to attack specific stages in the life cycle of HIV in T lymphocytes (De Clercq, Clin Microbiol Rev 1995; 8:200). In light of this, there currently are only two pharmacological strategies to win the war on AIDS. One of these is the use of reverse transcriptase inhibitors (both nucleoside and non-nucleoside) to block viral replication during the RNA reverse transcription to DNA (Cratlin et al., Virology 1998; 244:87). All of the nucleoside reverse transcriptase inhibitors are prodrugs that require intracellular metabolism to active triphosphate analogues (Lavie et al, Nature Med 1997, 3:922), and their use often results in drug resistance (Hazuda & Kuo, Nature Med 1997; 3:836). The other strategy involves inhibitors of HIV proteases responsible for processing of the gag and gag-pol polyproteins during virion maturation (Gulnik et al., Vit & Hormones. 2000; 58:213), but treatment with protease inhibitors also often results in drug resistance (Olsen et al., J Biol Chem 1999; 274:23699). The development of drug resistance is a major problem with antiretroviral drugs (Calvez, Antiviral Therapy 1998; 3(Suppl 4): 5).

In addition to classical drug designs based on the life cycle of the virus, there is another approach that is based on the immunobiology of T lymphocytes, which are the cells in AIDS patients that host the virus (Ho et al., Nature 1995; 373:123). Two recent studies suggest this is a promising approach. First, HIV-primed CD8 T lymphocytes have been shown to diminish viremia when transferred into AIDS patients (Drodic et al., Nature Med 1999; 5:34). Second, a caspase-3 proenzyme with an HIV protease activation site has been shown to activate apoptosis when transfected into HIV-infected T lymphocytes but not when transfected into uninfected cells (Vocero-Akbani et al., Nature Med 1995; 5:29). These reports suggest the possibility of controlling HIV infections by selectively killing the cells in which the virus lives.

An established observation about AIDS patients is that the immunodeficiency component of their disease is due to a deficiency of CD4 lymphocytes, which are the subpopulation of T lymphocytes in which HIV lives (Office of AIDS Research, Ann Intern Med 1998; 128:1057). The reason these cells are deficient in AIDS patients is that the virus initiates an enzymatically-mediated process of programmed cell death, which eliminates the cells by a reaction known as apoptosis (Cicala et al., Proc Natl Acad Sci USA 2000; 97:1178). When infected cells are killed by the virus, viremia increases, as measured by plasma HIV RNA levels (Report of NIH Panel, Ann Inern Med 1998; 128 (No. 12, pt 2): 1057), but when infected cells are killed by antiretroviral drugs, viremia decreases (Katzenstein et al., N Engl J Med 1996; 335:1091), and decreasing viremia is associated with improved clinical outcome (O'Brien et al., N Engl J Med 1996; 334:426).

Kast, et al., U.S. Pat. No. 6,242,176, discloses a method of delivering a pharmacologically active substance to a papillomavirus-infected cell. This method uses a complex including a pharmacologically active substance and a ligand recognizing CD16. The complex is exposed to the papillomavirus-infected cells under conditions sufficient for the ligand to bind CD16 on the cells. The pharmacologically active substance is thus brought into proximity to, and delivered to, the infected cell. The use of this method permits the targeted delivery of the pharmacologically active substance to the infected cells. This permits the employment of relatively high concentrations of many pharmacologically active agents to be delivered to the infected cells without many of the concomitant side effects attributed to the activity of such agents in noninfected cells.

The targeted delivery of drugs has the advantage of increasing efficacy while using less drug, thereby decreasing toxicity and causing less damage to normal cells, all of which effectively decrease costs and increase the quality of patient care. Targeted delivery also avoids drug-resistance, which is activated by the non-specific entrance of drugs into cells (Marbeuf-Gueye C, Ettori D, Priebe W, Kozlowski H and Garnier-Suillerot A. Correlation between the kinetics of anthracycline uptake and the resistance factor in cancer cells expressing the multidrug resistance protein or the P-glycoprotein. Biochem Biophy Acta 1999; 1450: 374-384). Because transferrin-drug conjugates enter cells specifically by employing a receptor-specific pathway (Klausner R D, vanReuswoude J, Ashwell G, Kempf C, Schechter A N, Dean A and Bridges K. Receptor-mediated endocytosis of transferrin in K562 cells. J Biol Chem 1983; 258: 4715-4724; Berczi A, Ruthner M, Szuts V, Fritzer M, Schweinzer E and Goldenberg H. Influence of conjugation of doxorubicin to transferrin on the iron uptake by K562 cells via receptor-mediated endocytosis. Euro J Biochem 1993; 213: 427-436), they are trafficked around drug-resistance mechanisms, such as efflux pumps in resistant cells.

SUMMARY OF THE INVENTION

The present invention provides a material for treating viral infections such as HIV, cytomegalovirus, adenovirus, hepatitis virus, and herpes simplex virus infections. The material comprises an infected cell targeting agent that binds with receptors up regulated by virally infected cells, such as transferrin or transcobalamin, conjugated with a component that inhibits the conjugate from leaving the cell after binding of the targeting agent with a receptor. The material has been found to induce apoptosis in cells infected with a virus. Suitable drugs include but are not limited to doxorubicin and methotrexate. The present invention also provides a method for treating patients infected with a virus and a composition containing the conjugate.

DETAILED DESCRIPTION OF THE INVENTION

The above discussed needs are filled by a conjugate for treating cells, especially stressed cells, that in one embodiment includes a carrier that is attracted to a receptor that is expressed in higher numbers or more frequently by cells under stress, conjugated with a material that effectively prevents the conjugated material from leaving the cell following binding between the carrier and a receptor that has been up regulated to the cell surface.

The carrier can be any useful material that is attracted to receptors on cells that present in higher numbers or more frequently when a cell is stressed. Preferably, the carrier is transferrin.

The agent may be any agent that accomplishes the purpose of increasing the affinity of the carrier for the receptor. The mechanism by which the affinity is increased may vary and may include, for example, attachment of the agent to phospholipids on the cell surface or steric reconfiguration of the carrier, provided that the effect of the mechanism is to interfere with the normal displacement of the carrier from the receptor after contact. The best known such agent at the moment is doxorubicin. However, any useful material that accomplishes the desired effect may be used.

Attachment of the agent to the carrier may be by any mechanism that prevents their separation, at least until after the carrier has been positioned in the corresponding receptor with increased affinity. Presently, the best known mechanism for attachment for the transferrin-doxorubicin conjugate is a gluteraldehyde linker, but it could be any useful material for the carrier/agent combination in question.

The present invention is based on the surprising and unexpected discovery that the well known transferrin-doxorubicin material that had been believed to deliver doxorubicin to cells for killing of the cell by normal doxorubicin toxicity mechanisms, such as DNA intercalation, does not, in fact, result in the cell being killed by that mechanism. It has been found that the cells treated by contact with the conjugate experience apoptotic type cell death rather than by necrosis as is found when cancer cells are treated with doxorubicin alone.

A fundamental aspect of the present invention is based on the observation that viremia decreases as the number of infected CD4 T lymphocytes are removed from the circulation (Betts et al., AIDS Res Hum Retrovir 1999; 15:1219), and that patient well being is increased as viremia decreases (Wenfurt et al., Medical Care 2000; 38:404). In light of this, one mechanism of lowering the viral load is via HIV-1-specific cytolytic CD8 T lymphocytes (Lubaki et al., J Acquir Imm Def Synd 1999; 22:19). Another mechanism to remove specific target cells is via the targeted delivery of protein conjugates of cytotoxic and/or antiretroviral drugs to cells that manifest a surface receptor for the carrier protein, as has been shown by using doxorubicin conjugates of human transferrin to kill human cancer cells that manifest transferrin receptors on their surfaces (Barabas et al., J Biol Chem 1992; 267:9437). Indeed, the binding reaction is so specific that doxorubicin conjugates of transferrin have been shown to bind isolated transferrin receptors even in the absence of cells (Ruthner et al., 1993; 54:35). In addition, the binding of transferrin-doxorubicin conjugates to transferrin receptors on cellular plasma membranes is more avid than the binding of unconjugated transferrin to transferrin receptors on cellular plasma membranes, probably because of additional interactions between the conjugate and constituents of the plasma membranes (Szuts et al., J Receptor Res 1993; 13:1041).

The present invention utilizes drug conjugates of human transferrin to be used in the targeted delivery of drugs to cells infected with viruses such as HIV. The primary reason that this invention is effective is that HIV-infected CD4 T lymphocytes up-regulate transferrin receptors to their surfaces (Ohno et al., Virology 1997; 238:305). However, there are several additional reasons why drug conjugates of transferrin are effective against HIV-infected T lymphocytes. First, many cytotoxic drugs, including doxorubicin (Ferraro et al., Cancer Res 2000; 60: 1901), induce apoptosis (Debatin, Tox Lett 2000; 112/113: 41), indicating that transferrin conjugates of doxorubicin are useful conjugates to induce apoptosis in cells with up-regulated transferrin receptors. Second, activation of transferrin receptors, by for instance transferrin-doxorubicin conjugates, is associated with drug-induced apoptosis (Leardi et al., Brit J Haematol 1998; 102:746), as well as with the control of calcium channels (Sainte-Marie et al., Eur J Biochem 1997; 250: 689-97) that are thought to be involved in effector pathways of apoptosis (Lepple-Wienhues et al., Proc Natl Acad Sci USA 1999; 96:13795; and Hueber, Nature Cell Biol 2000; 2: E23). Third, although transferrin receptors and apoptosis-inducing Fas receptors (APO-11/CD95) are located on the surface of cells (Findley & Zhou, Leukemia 1999; 13:147), when transferrin conjugates are delivered to cells with up-regulated transferrin receptors the conjugates are bound and eventually endocytosed (Berczi et al, Eur J Biochem 1993; 213:427), thus offering the possibility of killing by mechanisms activated at the cell surface as well as within the cell (Barabas et al., J Biol Chem 1992; 267:9437).

The immunobiology of purging T lymphocytes from the body is to initiate a pathway of programmed cell death by a process known as apoptosis (Pinkoski & Green, Cell Death & Dif 1999; 6: 1174-1181). This can occur in the thymus gland or in the peripheral circulation (Le Bon et al., Int Immunol 1999; 11: 373). Although there are several mechanisms of apoptosis, they all function to eliminate selected cells from the body (Martinez & Kraus, Int Rev Immunol 1999; 18: 527). The present invention is a novel way to eliminate HIV-infected T lymphocytes. The strategy of this approach is to eliminate the infected T lymphocytes by clonal deletion via apoptosis. This will be accomplished by using a drug-protein conjugate for the targeted delivery of cytotoxic and/or anti-retroviral drugs to infected cells.

Targeted delivery of the conjugate of this invention results from the protein in the conjugate having a binding affinity for receptors that are up-regulated to the surface of HIV-infected lymphocytes (Ohno et al., Virology 1997; 238:305). In addition, the drug in the drug-transferrin conjugate can be methotrexate, which is known to cause apoptosis and clonal deletion of activated peripheral T lymphocytes (Genestier et al., J Clin Invest 1998; 102: 322). Other than being present on the surfaces of cancer cells (Yeh et al., Vox Sang 1.984; 46: 217-223), infected cells (Ohno et al., Virology 1997; 238: 305) and antigen-stimulated T lymphocytes (Bayer et al., J Leukoc Biol 1998; 64: 19), transferrin receptors usually are not present on the surface or normal, adult, resting cells (Berczi et al., Arch Biochem Biophy 1993; 300: 356). Thus, normal cells will not be affected, and the only cells to be eliminated by a methotrexate-transferrin conjugate will be the infected T lymphocytes.

The way to realize this invention of targeted drug delivery to HIV infected cells is to focus on the use of transferrin, which carries iron in the blood. Transferrin can be obtained by isolation from blood plasma, from commercial suppliers, or from recombinant technology (Ali et al., J Biol Chem 1999; 274: 24066). To form the drug protein conjugate, the transferrin molecule must be modified in such a way as to prepare it to be coupled with a cytostatic or an antiretroviral drug. The drug can be an apoptosis initiator such as methotrexate, a cytotoxic antibiotic such as doxorubicin or an alkylating agent, but any compound can be used, including plant toxins such a ricin, and bacterial mutant toxins such as modified diptheria toxin (Laske et al., Nature Med 1997; 41: 1039). Several coupling processes such as glutaraldehyde coupling (Berczi et al., Arch Biochem Biophys 1993; 300: 356), disulfide coupling (Sasaki et al., Jap J Can Res 1993; 84: 191) and benzoyl hydrazone coupling (Kratz et al., J Pharm Sci 1998; 87: 338) have been used to couple transferrin with other compounds. The wide variety of coupling procedures allows the conjugation of a broad range of cytotoxic drugs to transferrin, resulting in either permanent or dissociable bonding of drugs with the transferrin molecule. Following the coupling reaction, drug-protein conjugates can be separated from uncoupled drug and free protein, preferably by using chromatographic procedures.

Technical details of the conjugation procedure can vary, but the requirement of any procedure is to prepare defined conjugates that are (a) active in binding and killing experiments with viral infected cells, and that (b) do not bind or kill significant numbers of normal cells. In light of these requirements, the preferred method for preparing the conjugates according to the present invention is the following process:

The synthesis of large amounts of homogeneous transferrin-adriamycin conjugates with predetermined molecular ratios was done stoichiometrically by employing the only amino group of doxorubicin (DOX), which is at the 3' amino position, to react with one of the two reactive groups on glutaraldehyde (GLU). Thus, the first step was drop-wise addition of a saline solution of DOX into a saline solution of GLU containing a solvent such as DMSO or another suitable cryopreservative, to a final concentration of a 1:1 molar ratio of DOX-to-GLU. The resulting solution of DOX-GLU was stirred three hours at room temperature in the dark.

The molarities of DOX and GLU were the same in the above reaction in order to produce a final solution of DOX-GLU that contains neither free DOX nor free GLU. However, there is the possibility of free GLU in solution if one GLU reacts with two DOX to produce DOX-GLU-DOX, but this possibility is minimized by the mass action kinetics generated by drop-wise addition of monovalent DOX into the solution of bivalent GLU. The volumes of these reactants are not restricted, so large amounts of homogeneous DOX-GLU can be prepared.

The second step in the conjugation reaction was drop-wise addition of DOX-GLU into a saline solution of transferrin (TRF). The TRF can be either iron-free (apo-transferrin) or iron-saturated (holo-transferrin). The desired molar ratio of DOX to TRF was obtained by appropriately adjusting the volume of TRF. The resulting solution of TRF-GLU-DOX was stirred for 20 hours at room temperature in the dark. Unlike the reaction of DOX with GLU, the reaction of DOX-GLU with TRF is not restricted to one binding site, for the GLU component of DOX-GLU can react with any one of several epsilon-amino lysine groups in the TRF molecule.

The number of DOX molecules bound to TRF was determined in the second step. For example, if the starting ratio of DOX-GLU to TRF was 7.2:1.0, the final solution of TRF-GLU-DOX would have contained 2.5 molecules of DOX per molecule of TRF. However, if the starting ratio of DOX-GLU to TRF was 4.0:1.0, the final solution of TRF-GLU-DOX would have contained 1,4 molecules of DOX per molecule of TRF. Similarly, if the starting ratio of DOX-GLU to TRF was 2.5:1.0, the final solution of TRF-GLU-DOX would have contained 0.9 molecules of DOX per molecule of TRF. In this way, large amounts of TRF-GLU-DOX with predetermined ratios of DOX-to-TRF can be provided according to the need.

Further steps in the conjugation reaction were the addition of ethanolamine or another substance suitable for scavenging any excess linker, followed by centrifugation and dialysis. Although reactions with DOX and TRF theoretically consume all of the GLU, ethanolamine was added to the final reaction mixture to bind any available GLU. This reaction was allowed to continue for 30 minutes in the dark. The final solution was centrifuged at 2000 rpm for 10 minutes, dialyzed twice for 6 hours in a 100-fold excess of saline and three times in the same excess of Hepes buffered saline, and the resulting TRF-GLU-DOX conjugates were ready for use.

Biochemical Characterization of the Conjugates:

By using HPLC and polyacrylamide gel electrophoresis as described in (39), the homogeneity of TRF-GLU-DOX conjugates can be determined. Also, by using spectrophotometry, the molecular ratio of DOX-to-TRF can be determined. These techniques repeatedly have revealed a consistent homogeneity of the TRF-GLU-DOX conjugates. In addition, chromatography is not required in the preparation of these conjugates, because there are no aggregates or fragments. This allows for the preparation of large volumes of homogeneous transferrin-drug conjugates, which increases yields and decreases costs.

The expenses caused by losses of TRF and DOX in other types of transferrin-drug conjugates have been an impediment to their use. For example, yields of DOX and TRF are decreased by using procedures such as thiolation that alter the drug and/or protein. Yields also are decreased by using solvent systems and by chromatography used to prepare acid-stable and acid-labile linkages. The GLU bond between DOX and TRF is acid-stable, and yields of useful conjugates prepared according to this invention are high. Indeed, compared to other procedures, the yield for useful conjugate is increased 5-fold. None of the previously known approaches to the preparation of transferrin-doxorubicin conjugates are capable of producing large amounts of homogeneous conjugates with predetermined ratios of the number of drug molecules per molecule of transferrin. In addition, the other approaches employ chromatography to eliminate aggregates and to harvest fractions that are enriched in homogeneous conjugates. These procedures decrease yields, increase costs, and lack the ability to predetermine molecular ratios.

Another procedure is to mix one milliliter or transferrin (0.5 mM) with one milliliter of doxorubicin (8.5 mM) in 150 mM sodium chloride for 4 minutes, and then add one milliliter of 21.5 mM glutaraldehyde in 150 mM sodium chloride and mix 4 minutes. The preceding reaction is a coupling procedure, which is stopped by the addition of 0.8 milliliters of 37.2 mM ethanolamine in 150 mM sodium chloride and 10 mM Hepes buffer (pH8) and vortexed for 4 minutes. The mixture then is transferred to dialysis tubing (molecular weight cutoff of 12,000-14,000) dialyzed against 0.5 liters of Hepes-buffered saline in the dark at 5° C. for 3 hours. The dialysis should be repeated at least once with fresh Hepes-buffered saline. The mixture then is centrifuged at 1600 g for 10-minutes at 4° C. and the supernatant is chromatographed at a flow rate of 22 milliliters per hour on a 2.6×34 cm column of Sepharose CL-4B, previously equilibrated in Hepes-buffered saline and calibrated at 5° C. with blue dextran, transferrin and cytochrome C. Elution from the column is monitored at 280 nm, and 3.8 milliliter fractions are collected. The concentration of transferrin and doxorubicin in each fraction is calculated by successive approximation from standard curves for transferrin and doxorubicin, determined by using 280 nm for transferrin and 295 nm for doxorubicin. With modifications, this coupling procedure can be used to prepare transferrin conjugates of other drugs, such as transferrin conjugates of methotrexate and/or antiretroviral drugs. Suitable antiretroviral drugs include but are not limited to nucleoside analogs, or nucleoside reverse transcriptase inhibitors (NRTIs), such as didanosine (ddI, Videx), lamivudine (3TC, Epivir), stavudine (d4T, Zerit), zalcitabine (ddC, Hivid), and zidovudine (AZT, Retrovir), non-nucleoside reverse transcriptase inhibitors (NNRTIs), such as delavirdine (Rescriptor), loviride, and nevirapine (Viramune), and Protease inhibitors, such as indinavir (Crixivan), nelfinavir (Viracept), ritonavir (Norvir) and saquinavir (Invirase).

When pure drug-protein conjugates are isolated, they can be characterized by polyacrylamide gel electrophoresis to determine their molecular weight, and the number of drug molecules per protein molecule can be determined. Experience with drug-protein conjugates in other systems has shown that a functional drug-protein ratio is 0.1-4.0 molecules of drug per molecule of protein (Berczi et al., Arch Biochem Biophy 1993; 300: 356). After conjugation, important steps in the characterization of the conjugates are to (a) determine if the conjugate binds to receptors on the surface of infected cells and not uninfected cells, and (b) determine if the conjugate kills infected cells and not uninfected cells. The binding studies can be done by using flow cytometry, and the killing studies can be done by using microculture techniques to determine the concentration of free drug required to kill 50% of a culture of infected cells compared to the concentration of drug in the drug-protein conjugate required to kill the same number of infected cells. Experience with drug-protein conjugates in other systems indicates that approximately 10-fold more free drug compared to the drug in drug-protein conjugates should be required to kill the same number of infected cells. For a conjugate to be efficacious, it also should kill only a minimum of uninfected cells.

While the present invention has been described in relation to transferrin being the delivery protein, it is known that other proteins exist in the body which are capable of binding to receptor sites on infected cells. If the receptor site is activated in infected cells, and is inactive in uninfected cells, then any protein or other compound which binds to such a receptor site can be used to deliver the drugs used in the present invention. One example of such a binding protein is transcobalamin, which delivers vitamins, especially vitamin B12, to transcobalamin receptors on cells in the human body (Seetheram, Ann Rev Nutr 1999; 19:173). Other examples include but are not limited to somatostatin, epidermal growth factor-like molecules and nonprotein targeting agents such as folic acid-like molecules.

After the drug-protein conjugate has been prepared, it can be purified, characterized and validated for cellular binding and killing properties, and, when the binding and killing experiments show that the conjugate binds to and kills infected cells but not uninfected cells, the conjugate can be aliquoted and sterilized. The sterilization process can be done by exposure to irradiation, such as by using a cesium irradiator, or it can be done by using Millipore filtration techniques.

According to a further aspect of the present invention, there is provided a reagent kit for the treatment of tumors, comprising iron-bearing transferrin and a conjugate of transferrin with an anti-viral agent. The patient's normal cells which have transferrin receptors may be protected against the effects of the conjugate by saturating these receptors with the iron-bearing transferrin before administration of the anti-viral agent.

The present invention also provides a process for determining the susceptibility of tumor cells to anti-viral agents, comprising administering separately to portions of infected cells, conjugates of transferrin with a number of different anti-viral agents. A reagent kit comprising a number of such different conjugates may be provided for this purpose.

The present invention also provides a composition where the conjugate is included in a "cocktail" which also includes at least one free (nonconjugated) anti-viral agent and a method for using the composition.

The conjugates according to the present invention are administered to an animal in an effective amount. In treating viral infections, an effective amount includes an amount effective to reduce the viral titer. The dosage for the conjugates can be determined taking into account the age, weight and condition of the patient and the pharmacokinetics of the anti-viral agent. The amount of the conjugate required for effective treatment will be less than the amount required using the anti-viral agent alone and depends upon the anti-viral agent used. For example, the dosage of a conjugate of transferrin-doxorubicin is expected to be between 0.5-50 mg per 28 day period for a 150 pound (68 kg) person. The dosage can be administered as smaller doses at varying intervals during the 28 day period.

The pharmaceutical compositions of the invention can be administered by a number of routes, including but not limited to orally, topically, rectally, ocularly, vaginally, by pulmonary route, for instance, by use of an aerosol, or parenterally, including but not limited to intramuscularly, subcutaneously, intraperitoneally, intra-arterially or intravenously. The compositions can be administered alone, or can be combined with a pharmaceutically-acceptable carrier or excipient according to standard pharmaceutical practice. For the oral mode of administration, the compositions can be used in the form of tablets, capsules, lozenges, troches, powders, syrups, elixirs, aqueous solutions and suspensions, and the like. For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. For pulmonary administration, diluents and/or carriers will be selected to be appropriate to allow the formation of an aerosol. It is preferred that the conjugate of the present invention be administered parenterally, i.e. intravenously or intraperitoneally, by infusion or injection.

Preferred embodiments of the present invention are described below. It will be apparent to those of ordinary skill in the art after reading the following description that modifications and variations are possible, all of which are intended to fall within the scope of the claims.

EXAMPLE 1

Preparation of Homogeneous Conjugates

The synthesis of large amounts of homogeneous transferrin-doxorubicin conjugates with predetermined molecular ratios was done stoichiometrically by employing the only amino group of doxorubicin (DOX), which is at the 3' amino position, to react with one of the two reactive groups on glutaraldehyde (GLU). The first step was to add GLU drop-wise to DMSO in an ice cold water bath. Next was the drop-wise addition of a saline solution of DOX into a saline solution of GLU+DMSO to a final concentration of a 1:1 molar ratio of DOX-to-GLU. The resulting solution of DOX-GLU was stirred three hours at room temperature in the dark.

The molarities of DOX and GLU were the same in the above reaction in order to produce a final solution of DOX-GLU that contains neither free DOX nor free GLU. However, there is the possibility of free GLU in solution if one GLU reacts with two DOX to produce DOX-GLU-DOX, but this possibility is minimized by the mass action kinetics generated by drop-wise addition of monovalent DOX into the solution of bivalent GLU. The volumes of these reactants are not restricted, so large amounts of homogeneous DOX-GLU can be prepared.

The second step in the conjugation reaction was drop-wise addition of DOX-GLU into a saline solution of transferrin (TRF). The TRF can be either iron-free (apo-transferrin) or iron-saturated (holo-transferrin). The desired molar ratio of DOX to TRF was obtained by appropriately adjusting the volume of TRF. The resulting solution of TRF-GLU-DOX was stirred for 20 hours at room temperature in the dark. Unlike the reaction of DOX with GLU, the reaction of DOX-GLU with TRF is not restricted to one binding site, for the GLU component of DOX-GLU can react with any one of several epsilon-amino lysine groups in the TRF molecule.

The number of DOX molecules bound to TRF was determined in the second step. For example, if the starting ratio of DOX-GLU to TRF was 7.2:1.0, the final solution of TRF-GLU-DOX would have contained 2.5 molecules of DOX per molecule of TRF. However, if the starting ratio of DOX-GLU to TRF was 4.0:1.0, the final solution of TRF-GLU-DOX would have contained 1.4 molecules of DOX per molecule of TRF. Similarly, if the starting ratio of DOX-GLU to TRF was 2.5:1.0, the final solution of TRF-GLU-DOX would have contained 0.9 molecules of DOX per molecule of TRF. In this way, large amounts of TRF-GLU-DOX with predetermined ratios of DOX-to-TRF can be provided according to the need.

Further steps in the conjugation reaction were the addition of ethanolamine, followed by centrifugation and dialysis. Although reactions with DOX and TRF theoretically consume all of the GLU, ethanolamine was added to the final reaction mixture to bind any available GLU. This reaction was allowed to continue for 30 minutes in the dark. The final solution was centrifuged at 2000 rpm for 10 minutes, dialyzed twice for 6 hours in a 100-fold excess of saline and three times in the same excess of Hepes buffered saline, and the resulting TRF-GLU-DOX conjugates were ready for use. Biochemical Characterization of the Conjugates:

By using HPLC and polyacrylamide gel electrophoresis, the homogeneity of TRF-GLU-DOX conjugates can be determined. Also, by using spectrophotometry, the molecular ratio of DOX-to-TRF can be determined. These techniques repeatedly have revealed a consistent homogeneity of the TRF-GLU-DOX conjugates. In addition, chromatography is not required in the preparation of these conjugates, because there are no aggregates or fragments. This allows for the preparation of large volumes of homogeneous transferrin-drug conjugates, which increases yields and decreases costs.

The expenses caused by losses of TRF and DOX in other types of transferrin-drug conjugates have been an impediment to their use. For example, yields of DOX and TRF are decreased by using procedures such as thiolation that alter the drug and/or protein. Yields also are decreased by using solvent systems and by chromatography used to prepare acid-stable and acid-labile linkages. The GLU bond between DOX and TRF is acid-stable, and yields of DOX and TRF in TRF-DOX conjugates prepared according to this invention are high. Indeed, compared to other known procedures, the yield for TRF is nearly doubled (90% vs 50%), and the yield for DOX is increased 5-fold.

None of the previously known approaches to the preparation of transferrin-doxorubicin conjugates are capable of producing large amounts of homogeneous conjugates with predetermined ratios of the number of drug molecules per molecule of transferrin. In addition, the other approaches employ chromatography to eliminate aggregates and to harvest fractions that are enriched in homogeneous conjugates. These procedures decrease yields, increase costs, and lack the ability to predetermine molecular ratios.

EXAMPLE 2

Anti-Viral Activity

The effectiveness against different viruses was studied. These were Cytomegalovirus (CMV), Hepatitis B virus (HBV) and HIV. The results versus HIV were particularly good.

Figure 1:
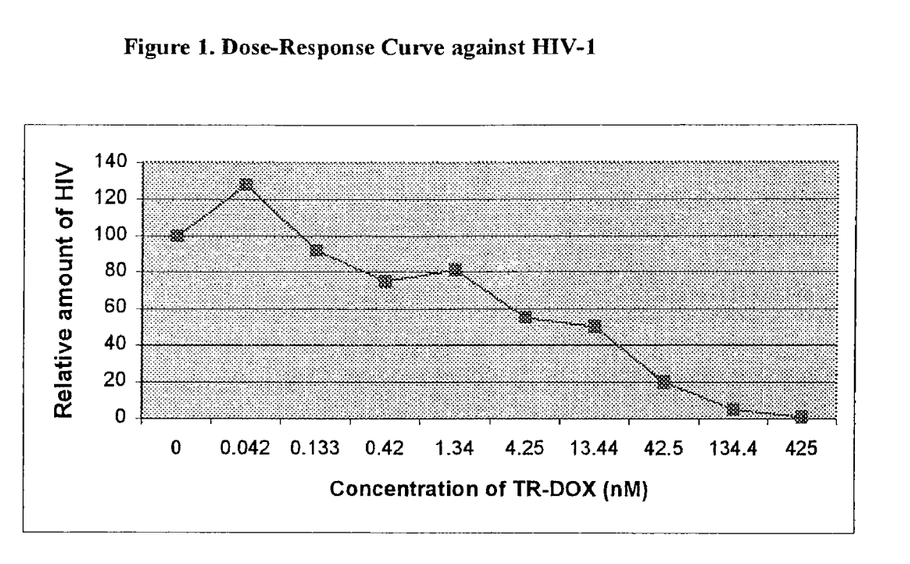
FIG. 1 shows the dose-response curve obtained for the inhibition of the ROJO strain of HIV-1 virus living in human blood cells by a transferrin-doxorubicin (TR-DOX) conjugate.

For example, the dose-response curve obtained for the inhibition of the ROJO strain of HIV-1 virus living in human blood cells by TR-DOX is shown in FIG. 1. In this laboratory test system, the TR-DOX clearly had a powerful effect on the AIDS virus at concentrations which suggest that TR-DOX could be used as an effective drug to treat HIV in human AIDS patients.

Figure 2:
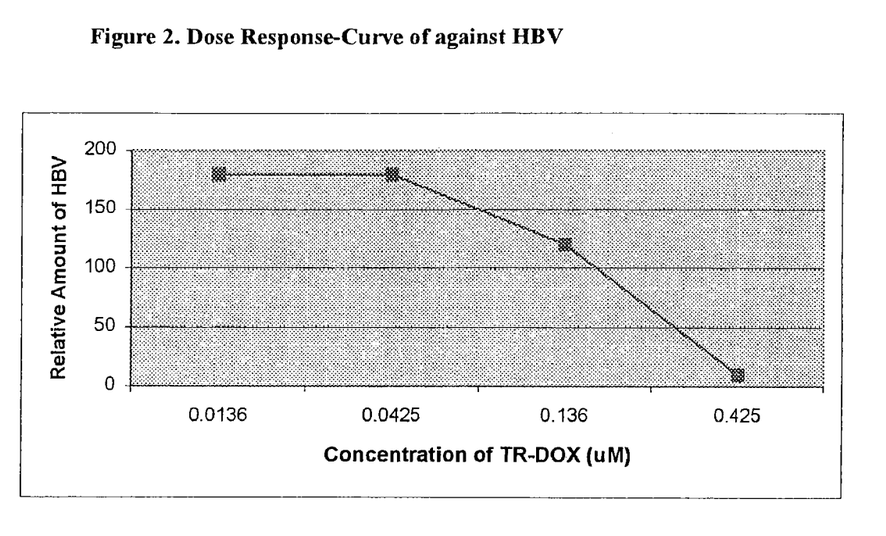
FIG. 2 shows the dose response curve obtained by exposing human liver cells infected with Hepatitis B virus (HBV) to increasing concentrations of a transferrin-doxorubicin (TR-DOX) conjugate.

Similarly, FIG. 2 shows the dose-response curve obtained by exposing human liver cells infected with Hepatitis B virus (HBV) to increasing concentrations of TR-DOX. Once again, very low concentrations of TR-DOX were found to cause an almost complete inhibition of the HBV.

Figure 3:
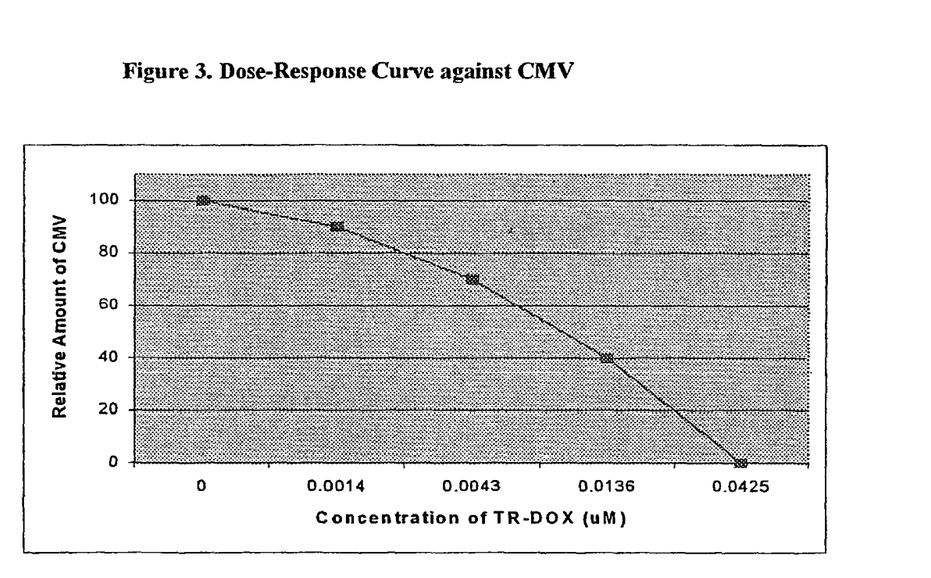
FIG. 3 shows the effect of a transferrin-doxorubicin (TR-DOX) conjugate on Cytomegalovirus (CMV) living in human lung cells.

Finally, the effect of TR-DOX on Cytomegalovirus (CMV) living in human lung cells was studied, and once again the data revealed a potent effect of TR-DOX against CMV. The dose-response curve for TR-DOX against CMV is shown below in FIG. 3.

When the relative potency of TR-DOX against CMV was directly compared with the potency of Ganciclovir (which is a widely used anti-viral compound), it was found that TR-DOX was over 200-fold more potent than Ganciclovir in terms of the concentration required to inhibit CMV by 50%.

The invention claimed is:

1. A method for inducing apoptosis in a cell infected with a virus, comprising
administering to said cell an effective amount of a conjugate containing transferrin and doxorubicin and wherein said transferrin and said anti-viral drug are linked via a glutaraldehyde linker, and wherein said conjugate induces apoptosis of said cell infected with a virus.

2. The method according to claim 1, wherein said virus is selected from the group consisting of human immunodeficiency virus, cytomegalovirus, and hepatitis virus.

3. The method according to claim 2, wherein said virus is human immunodeficiency virus.

4. A method for inducing apoptosis in a patient infected with a virus, comprising administering to a cell infected with a virus in said patient, a conjugate containing a targeting agent and an anti-viral agent, wherein said anti-viral agent is doxorubicin, said targeting agent is transferrin, and wherein said targeting agent and said anti-viral agent are linked via a glutaraldehyde linker, and wherein said conjugate induces apoptosis of said cell infected with a virus.

5. The method according to claim 4, further comprising administering iron bound transferrin prior to administering said conjugate.

6. The method according to claim 4, wherein said virus is selected from the group consisting of human immunodeficiency virus, cytomegalovirus, and hepatitis virus.

7. The method according to claim 6, wherein said virus is human immunodeficiency virus.

8. The method according to claim 4, further comprising administering a nonconjugated antiviral agent.

* * * * *